United States Patent [19]

den Braber

[11] Patent Number: 4,464,308
[45] Date of Patent: Aug. 7, 1984

[54] PROCESS FOR PREPARING DIMETHYL β,β-DICHLOROVINYLPHOSPHATE

[75] Inventor: Antonie A. den Braber, Putten, Netherlands

[73] Assignee: Denka Chemie B.V., Vorrthuizen, Netherlands

[21] Appl. No.: 390,692

[22] Filed: Jun. 21, 1982

[30] Foreign Application Priority Data

Jul. 6, 1981 [NL] Netherlands .......................... 8103227

[51] Int. Cl.³ ............................................. C07F 9/40
[52] U.S. Cl. .................................... 260/969; 260/956
[58] Field of Search ................................ 260/969, 957

[56] References Cited

U.S. PATENT DOCUMENTS 2,765,331 10/1956 Whetstone et al. ................ 260/957
2,956,073 10/1960 Whetstone et al. ................ 260/957
3,116,201 12/1963 Whetstone et al. ................ 260/969

Primary Examiner—Anton H. Sutto
Attorney, Agent, or Firm—Murray Schaffer

[57] ABSTRACT

A process for preparing dimethyl β,β-dichlorovinylphosphate is provided by reaction of chloral with trimethylphosphite at atmospheric pressure, wherein, for completing the reaction, the reaction mixture is heated at a temperature of 150°–210° C. during at least 10 seconds.

3 Claims, No Drawings

PROCESS FOR PREPARING DIMETHYL β,β-DICHLOROVINYLPHOSPHATE

This invention relates to a process for preparing dimethyl β,β-dichlorovinylphosphate by reacting chloral with trimethylphosphite at atmospheric pressure.

This reaction has been disclosed in U.S. Pat. No. 2,956,073 for a somewhat larger group of compounds. For this group it has been indicated generally in column 6, lines 42 a.f. that reaction temperatures of 10°–150° C. or higher can be used and that the reaction is exothermic and in some cases may proceed vigorously, whereafter it is mentioned that one may cause the reaction to proceed at a desired temperature with the aid of various means. There is nothing from which appears that a temperature of 150° C. or higher would ever have been used according to this U.S. patent in the reaction of chloral with trimethylphosphite. On the contrary, in all working examples, wherein reactions of chloral with phosphite esters are disclosed, relatively low reaction temperatures are maintained; in the case of Example V, the only example which discloses the present reaction, a reaction temperature of 48°–55° C. is maintained by cooling. After the mixture has been standing overnight, it is then distilled at reduced pressure.

The reaction is also disclosed in Berichte 87, 755–758 (1954). In that case the general prescription is that chloral is added slowly with stirring and cooling with ice to the trialkylphosphite which has been diluted with ether or benzene, while keeping the reaction temperature below 20° C. Also here the product is then distilled under reduced pressure.

The vacuum distillation for recovering the product was a logical necessity in both publications in order to identify the then still novel product. In the meantime the dimethyl(β,β-dichlorovinyl)phosphate has been well accepted in the commercial practice as an insecticide and of course it is then important to have at one's disposal a process, whereby on a commercial scale a product of sufficient purity can be obtained to be used as a commercial product. According to Dutch Pat. No. 129,880 a highly pure product is obtained in a very high yield by reacting the chloral and the trimethylphosphite in the absence of a solvent at a temperature below 40° C. and a pressure of no more than 2.67 kPa. Indeed excellent results are obtained with this process in the laboratory. However, for commercial practice this expedient entails even worse drawbacks, for the carrying out of the entire reaction under reduced pressure and at a low temperature means that the preparation always involves a large energy consumption for the necessary cooling bath and the necessary vacuum and that working on a commercial scale should considered practically excluded, while also a continuous process is impossible. Consequently, the working example of patent No. 129,880 relates to a laboratory experiment which is carried out in a round bottom flask of 500 ml.

Australian patent application No. 11980/70 discloses a process for preparation of O,O-dimethyl-2,2-dichlorovinylphosphate by reacting chloral and trimethylphosphite without solvents, the only dilution being the final product from previous preparations initially and the product gradually produced in the reaction. The reaction mixture is kept at temperatures between 25° C. and 50° C. until suitable quantities of the reagents have been brought together, i.e. until the reaction is substantially completed. Thereafter the product may be heated up to 100° C. for complete degasification, and it is mentioned explicitly that for better results vacuum is applied, but only for the removal of gases formed during the reaction. Thus, this Australian patent application is based on the understanding that for obtaining a product of commercial quality the reaction can be carried out with somewhat less caution than according to the other above-mentioned processes. However, still temperatures higher than 100° C. are avoided and vacuum is still said to improve the final result.

A principal object of the present invention is to provide a process for preparing dimethyl β,β-dichlorovinylphosphate through the reaction of chloral with dimethylphosphite which produces a high quality commercial product without undue energy consumption due to cooling and vacuum and without the complications caused by such measures.

Further objects will appear from the following description of the invention.

Surprisingly, it has now been found that during the last phase of the present reaction a temperature of 150° C. or higher at atmospheric pressure is permissible and that this has the advantage that thereby the side-products, in the first place methylchloride, are removed to a large extent. Accordingly, by using this understanding a preparation on a commercial scale is possible, and the so obtained product is sufficiently pure for its normal use.

According to the invention a process is provided for preparing dimethyl β,β-dichlorovinylphosphate by reacting chloral with trimethylphosphite at atmospheric pressure, wherein for completing the reaction the mixture is heated at a temperature of 150°–210° C. during at least 10 seconds.

With the aid of this process, and without further measures or aftertreatment a product can be obtained which satisfies the commercial purity requirements (95%) or even possesses a higher degree of purity. Furthermore, an important advantage of the novel process is that it can be carried out not only batch-wise, but also continuously.

Due to the heating applied towards the end of the reaction, which is contrary to the understandings existing up till now, not only the principal side-product, methylchloride, is drastically eliminated, but apparently also other impurities.

The temperature at which this heat treatment is carried out should be at least 150° C., because otherwise the desired effect is not obtained to a sufficient degree. Above 210° C. side reactions will occur to a too large extent so that this upper limit should not be exceeded.

Of course, the time of the heat treatment will depend somewhat on the chosen temperature. A minimum of 10 seconds is necessary. A clear upper limit cannot be indicated. Of course, a too long time at a high temperature will lead to a decrease of the yield and/or degree of purity due to side-reactions, but this effect is not great and in general time periods up to 50 seconds can be tolerated. Of course this is also dependent on the question whether one works batch-wise or continuously and in the last case it depends also on the volume of the feed.

Of course, before the heat treatment the reaction should have been carried out already for a part. This means that before the heat treatment a reaction time of at least 10 seconds should have elapsed and preferably a reaction time of 25 seconds or more. An upper limit for this reaction time at lower temperature actually does not exist. The real reaction time in each case will be determined by practical considerations, also dependent on the used apparatus. This first part of the reaction can be carried out at any temperature below 150° C. The exact temperature chosen will also depend on the available cooling agents and economy.

It is possible that the two reaction components have already been admixed completely before the temperature is increased to at least 150° C., or a part of one of the reaction components (generally the trimethylphosphite) can be added only during this heat treatment. Resuming, it can be stated that within the scope of the invention there is great liberty in choosing the reaction conditions, provided the completing of the reaction is carried out in the above-mentioned way.

The invention is illustrated hereinbelow with the aid of the following examples of some embodiments, to which, however, the invention is not limited.

EXAMPLE 1

160 liters of chloral were introduced into a jacketed reaction vessel of 500 liters, and trimethylphosphite was added gradually and continuously, care being taken that the temperature during the addition of the first 175 liters was always kept between 60° C. and 120° C. by circulating ice-water through the cooling jacket. Thereafter, the cooling bath was removed and the mixture was allowed to warm to about 180° C. by the exotherm, as a further 35 liters of trimethylphosphite were added. During the entire reaction the vapors exiting from the reaction vessel were removed through a condensor. The dimethyl $\beta,\beta$-dichlorovinylphosphate was obtained in a yield of over 90% and it had a degree of purity of 96%.

EXAMPLE 2

A tubular reactor having a volume of about 100 liters was used for a continuous reaction. The reactor had a diameter of 20 cm and a length of about 3.2 m. Over about ⅔ of its length the reactor was provided with a cooling jacket, through which the cooling water flowed in the same direction as the reaction components so that the cooling effect was strongest at the beginning of the reaction. Furthermore, an internal cooling element was provided at a distance of about 0.8 m from the inlet side of the reactor, in order to cool the mixture further, if necessary. The inlet side of the horizontally placed reactor was provided with lines for introducing trimethylphosphite and chloral and the outlet side was provided with a vapor outlet and an outlet for the product. Per hour about 105 liters of trimethylphosphite and about 80 liters of chloral were introduced. In the first third part of the reactor the temperature, which was measured with thermo-elements, was not allowed to rise above 120° C.; in the middle third part of the reactor the mixture attained a temperature of about 145° C. and in the last part of the reactor the temperature rose to about 195° C. The product taken from the reactor was passed through a condensor before being received. The yield of this continuous reaction was almost quantitative and the degree of purity of the product was 97%, and the reaction could be continued for a substantially unlimited time.

What is claimed is:

1. A process for preparing dimethyl $\beta,\beta$-dichlorovinylphosphate comprising the steps of partially reacting chloral with trimethylphosphite at atmospheric pressure and at a temperature not execeeding 150° C., and thereafter heating the mixture at a temperature of between 150°–210° C. for at least 25 seconds and until the reaction of said chloral and trimethylphosphite is completed.

2. Process according to claim 1, wherein the step of heating the mixture at 150°–210° C. is carried out during the last third part of the reaction time.

3. A process according to claim 1, wherein the total minimum time for mixture and completion of the reaction is 35 seconds.

* * * * *